United States Patent
Rao et al.

(10) Patent No.: US 8,715,177 B2
(45) Date of Patent: May 6, 2014

(54) INTELLIGENT DRUG DELIVERY APPLIANCE

(75) Inventors: Raman K. Rao, Palo Alto, CA (US); Sanjay K. Rao, Palo Alto, CA (US)

(73) Assignee: IP Holdings, Inc., Palo Alto, CA (US)

(*) Notice: Subject to any disclaimer, the term of this patent is extended or adjusted under 35 U.S.C. 154(b) by 966 days.

(21) Appl. No.: 11/708,269

(22) Filed: Feb. 20, 2007

(65) Prior Publication Data
US 2012/0190955 A1 Jul. 26, 2012

Related U.S. Application Data

(63) Continuation of application No. 11/018,862, filed on Dec. 19, 2004, and a continuation-in-part of application No. 11/001,668, filed on Nov. 30, 2004.

(51) Int. Cl.
A61B 5/00 (2006.01)
A61M 31/00 (2006.01)

(52) U.S. Cl.
USPC ............ 600/300; 600/301; 600/365; 604/503

(58) Field of Classification Search
USPC .................. 600/300, 301; 128/903–905, 920
See application file for complete search history.

(56) References Cited

U.S. PATENT DOCUMENTS

| | | |
|---|---|---|
| 4,465,401 A | 8/1984 | Stoddord et al. |
| 4,675,401 A | 6/1987 | Robin |
| 4,675,653 A | 6/1987 | Priestly |
| 5,195,130 A | 3/1993 | Weiss et al. |
| 5,242,382 A | 9/1993 | Gorsuch et al. |
| 5,379,341 A | 1/1995 | Wan |
| 5,410,738 A | 4/1995 | Diepstraten et al. |
| 5,465,401 A | 11/1995 | Thompson |
| 5,513,242 A | 4/1996 | Mukerjee et al. |
| 5,517,553 A | 5/1996 | Sato |
| 5,539,391 A | 7/1996 | Yuen |
| 5,551,953 A | 9/1996 | Lattin et al. |
| 5,555,258 A | 9/1996 | Snelling et al. |
| 5,559,794 A | 9/1996 | Willis et al. |
| D374,675 S | 10/1996 | Sakai et al. |
| 5,565,929 A | 10/1996 | Tanaka |
| 5,566,205 A | 10/1996 | Delfine |

(Continued)

FOREIGN PATENT DOCUMENTS

WO WO 92/03884 3/1992

OTHER PUBLICATIONS

U.S. Appl. No. 09/680,611, filed Oct. 6, 2000 in the name of Rao et al., Non-Final Office Action mailed Aug. 8, 2002.

(Continued)

*Primary Examiner* — Bill Thomson
*Assistant Examiner* — Shirley Jian
(74) *Attorney, Agent, or Firm* — Levine Bagade Han LLP

(57) ABSTRACT

A system, method and apparatus for real time measurement and monitoring of various personal health parameters including controlled delivery of drugs/medications by intelligent pump appliances, intelligent inhalation appliances and intelligent skin patch appliances used in a standalone manner or in a wired or wireless networked configuration, in conjunction with various peripheral devices, other intelligent appliances, servers, RF ID Tags and stationary/mobile devices. The intelligent appliances relate to the measurement, monitoring and delivery of insulin/other drugs for the treatment of diabetes and other diseases. The method also additionally includes the application of intelligent appliances for pain management including visualization of organs and body locations exhibiting pain.

30 Claims, 5 Drawing Sheets

(56) References Cited

U.S. PATENT DOCUMENTS

| | | | |
|---|---|---|---|
| 5,577,118 | A | 11/1996 | Sasaki et al. |
| 5,672,154 | A | 9/1997 | Sillen et al. |
| 5,741,317 | A | 4/1998 | Ostrow |
| 5,845,263 | A | 12/1998 | Camaisa et al. |
| 5,860,957 | A | 1/1999 | Jacobsen et al. |
| 5,862,803 | A | 1/1999 | Besson et al. |
| 5,980,934 | A | 11/1999 | Reber et al. |
| 6,139,495 | A | 10/2000 | De La Huerga |
| 6,175,752 | B1 | 1/2001 | Say et al. |
| 6,219,638 | B1 | 4/2001 | Padmanabahan et al. |
| 6,314,405 | B1 | 11/2001 | Richardson |
| 6,425,524 | B2 | 7/2002 | Pentel |
| 6,527,712 | B1 | 3/2003 | Brown et al. |
| 6,540,672 | B1* | 4/2003 | Simonsen et al. ............ 600/300 |
| 6,553,244 | B2 | 4/2003 | Lesho et al. |
| 6,579,231 | B1 | 6/2003 | Phipps |
| 6,599,241 | B1 | 7/2003 | Murphy |
| 6,629,776 | B2 | 10/2003 | Bell et al. |
| 6,662,051 | B1 | 12/2003 | Eraker et al. |
| 6,690,397 | B1 | 2/2004 | Daignault |
| 6,771,995 | B2 | 8/2004 | Kurnik et al. |
| 6,814,706 | B2 | 11/2004 | Barton et al. |
| 6,865,261 | B1 | 3/2005 | Rao et al. |
| 7,009,511 | B2 | 3/2006 | Mazar et al. |
| 7,237,717 | B1* | 7/2007 | Rao et al. ...................... 235/386 |
| 7,356,705 | B2 | 4/2008 | Ting |
| 2001/0053987 | A1 | 12/2001 | Kleinschmidt et al. |
| 2002/0019584 | A1 | 2/2002 | Schulze et al. |
| 2002/0126036 | A1 | 9/2002 | Flaherty et al. |
| 2002/0147135 | A1 | 10/2002 | Schnell |
| 2003/0149343 | A1 | 8/2003 | Siegel et al. |
| 2003/0208113 | A1 | 11/2003 | Mault et al. |
| 2004/0003256 | A1 | 1/2004 | Coffy et al. |
| 2004/0039255 | A1* | 2/2004 | Simonsen et al. ............ 600/300 |
| 2004/0073095 | A1* | 4/2004 | Causey et al. ................. 600/300 |
| 2004/0102931 | A1 | 5/2004 | Ellis et al. |
| 2004/0176674 | A1 | 9/2004 | Nazeri |
| 2005/0003470 | A1 | 1/2005 | Nelson et al. |
| 2005/0010087 | A1* | 1/2005 | Banet et al. ................... 600/300 |
| 2005/0010435 | A1* | 1/2005 | Kato et al. ........................ 705/2 |
| 2005/0038674 | A1* | 2/2005 | Braig et al. ....................... 705/2 |
| 2005/0076909 | A1 | 4/2005 | Stahmann et al. |
| 2005/0080322 | A1 | 4/2005 | Korman |
| 2005/0080652 | A1* | 4/2005 | Brown ............................... 705/2 |
| 2005/0192557 | A1* | 9/2005 | Brauker et al. ............... 604/503 |
| 2005/0197554 | A1 | 9/2005 | Polcha |
| 2005/0251424 | A1 | 11/2005 | Sanders et al. |
| 2005/0277872 | A1 | 12/2005 | Colby, Jr. et al. |
| 2006/0004263 | A1 | 1/2006 | Feliss et al. |
| 2006/0004271 | A1 | 1/2006 | Peyser et al. |
| 2006/0036134 | A1* | 2/2006 | Tarassenko et al. .......... 600/300 |
| 2007/0060796 | A1* | 3/2007 | Kim ............................... 600/300 |
| 2007/0106133 | A1* | 5/2007 | Satchwell et al. ............ 600/309 |
| 2008/0139907 | A1 | 6/2008 | Rao et al. |
| 2008/0191866 | A1 | 8/2008 | Falck et al. |

OTHER PUBLICATIONS

U.S. Appl. No. 09/680,611, filed Oct. 6, 2000 in the name of Rao et al., Final Office Action mailed Apr. 22, 2003.
U.S. Appl. No. 09/680,611, filed Oct. 6, 2000 in the name of Rao et al., Non-final Office Action mailed Jan. 15, 2004.
U.S. Appl. No. 09/680,611, filed Oct. 6, 2000 in the name of Rao et al., Notice of Allowance mailed Sep. 23, 2004.
U.S. Appl. No. 09/680,611, filed Oct. 6, 2000 in the name of Rao et al., Notice of Allowance mailed Feb. 4, 2005.
U.S. Appl. No. 11/708,282, filed Feb. 20, 2007 in the name of Rao et al., Non-final Office Action mailed Jun. 1, 2010.
U.S. Appl. No. 11/708,282, filed Feb. 20, 2007 in the name of Rao et al., Final Office Action mailed Feb. 28, 2011.
U.S. Appl. No. 11/708,395, filed Feb. 20, 2007 in the name of Rao, Non final Office Action mailed Sep. 18, 2009.
U.S. Appl. No. 11/708,395, filed Feb. 20, 2007, in the name of Rao, Final Office Action mailed Jun. 18, 2010.
U.S. Appl. No. 11/001,668, filed Nov. 20, 2004 in the name of Rao et al., Non-final Office Action mailed Apr. 9, 2007.
U.S. Appl No. 11/001,668, filed Nov. 20, 2004 in the name of Rao et al., Final Office Action mailed Jul. 24, 2007.
U.S. Appl. No. 11/001,668, filed Nov. 20 2004 in the name of Rao et al., Final Office Action mailed Sep. 27, 2007.
U.S. Appl. No. 11/001,668, flied Nov. 20, 2004 in the name of Rao et al., Final Office Action mailed Jul. 9, 2008.
U.S. Appl. No. 11/001,668, filed Nov. 20, 2004 in the name of Rao et al., Final Office Action mailed Mar. 6, 2009.
U.S. Appl. No. 11/001,668, filed Nov. 20, 2004 in the name of Rao et al., Final Office Action mailed Nov. 1, 2010.
U.S. Appl. No. 11/018,862, filed Dec. 19, 2004, in the name of Rao et al., Non-Final Office Action mailed Jun. 9, 2010.
U.S. Appl. No. 11/018,862, filed Dec. 19, 2004, in the name of Rao et al., Final Office Action mailed Oct. 13, 2010.

* cited by examiner

PERSONAL HEALTH MANAGEMENT RECORD -1

NAME OF INDIVIDUAL:     PRIMARY PHYSICIAN:     HOSPITAL:     INSURANCE CARRIER:

SS NUMBER:     RFID:     MOBILE DEVICE ID:     APPLIANCE ID:     CENTRAL SERVER ID:

EMERGENCY CONTACT INFORMATION:                         ESCROW SERVER ID:

| Date/Time | BG Level | Food Ingestion Type, Qty Location | Medications Type and Qty Ingested | Physical Activity Type and Duration | Health Symptoms Type and Duration | Insulin Infusion Levels | Action Taken |
|---|---|---|---|---|---|---|---|
| 1/1/05<br>0000<br>0100<br>0200<br>0300<br>0400<br>0500<br>0600<br>0700<br>0800<br>0900<br>1000<br>1100<br>1200<br>1300<br>1400<br>1500<br>1600<br>1700<br>1800<br>1900<br>2200<br>2100<br>2200<br>2300<br>2400 | | | | | | | |
| 1/2/05 | | | | | | | |
| 1/3/05 | | | | | | | |
| 1/4/05 | | | | | | | |
| XX/YY/ZZ | | | | | | | |

FIG. 5

INTELLIGENT DRUG DELIVERY APPLIANCE

CROSS REFERENCE TO RELATED APPLICATIONS

This application is a continuation of U.S. patent application Ser. No. 11/018,862, filed Dec. 19, 2004, and a continuation in part application of application titled "Secure system for Real time personal health management using mobile intelligent appliances and gastronomic information," U.S. patent application Ser. No. 11/001,668, filed Nov. 30, 2004.

ABBREVIATIONS

Cellular Telephone is abbreviated as CT
Mobile Device is abbreviated as MD
Intelligent Personal Health Management Appliance is abbreviated as IPHMA
Personal Health Management is abbreviated as PHM
Intelligent Skin Patch System is abbreviated as ISPS
Intelligent Activated Skin Patch System is abbreviated as IASPS
The terms Appliance and Device are used interchangeably.
The usage of the word drug refers to medications approved by regulatory bodies for consumption by individuals.

BACKGROUND OF THE INVENTION

There is a need for a new class of intelligent appliances, referred in here as intelligent personal health management appliances, that enable the individual to personally acquire one or more types of biological information in real time, archive said information for correlation with factors such as diet and other activities including physical exercise/mental activity/stress and other factors, for personal health management by the individual him/her self or for personal health management in conjunction with a qualified health professional. The present invention teaches novel methods and novel appliances for real time data acquisition of biological information, for archiving said data for contemporaneous utility or for utility at a selected time, for analyzing said data, for determining trends, for communication of said data/trends to one or more health professionals and for comprehensive real time management of the personal health of an individual in a cost effective manner in accordance with the quality/cost objectives acceptable to the individual.

Specifically, the present invention relates to intelligent appliances for monitoring the blood sugar level of an individual for management of diabetes and related health factors. The incidence of both adult diabetes and pediatric/juvenile diabetes is increasingly rapidly in most populations as a result of improper diet and lack of exercise. The blood glucose level is a proven indicator for measuring the level of diabetes. The level of blood glucose in the blood stream is well co-relatable with the ingestion of various foods, the time from the ingestion of various foods, the frequency and amount of ingestion of different foods; and also the level of physical activity.

While genetics plays a role in determining whether an individual has a high probability for being afflicted with diabetes, the onset of diabetes and the severity of diabetes are controllable by following certain norms of controllable behavior. Neglecting to diagnose, treat and control diabetes may lead to nerve disease, kidney disease, retinal eye disease and in some cases loss of limbs such as toes.

The healthy human body actively controls the level of blood glucose levels by regulating the amount of insulin production, wherein the insulin is generated by the pancreas. The treatment of diabetes requires that the level of insulin within the body is monitored and managed actively by helping the pancreas generate proper levels of insulin internal to the human body or providing controlled amounts of insulin delivered in a programmed manner from external sources, in conjunction with the ingestion of food/dietary habits that is best suited to a specific individual.

Therefore, there is a need for blood glucose monitoring appliances and also for insulin delivery appliances to regulate the blood glucose level within the human body. The prior art equipment/devices for monitoring blood glucose levels and or delivery of insulin from sources external of the body, such as through a catheter inserted into the fatty tissue of the body, suffer from a number of limitations which include; inability to automate, inability for real time measurement and tracking, inability for measurement and delivery on the move, inability for continuous or programmed delivery of insulin in a manner specific to the individual, in ability to relate diet and exercise in real time to the levels of blood glucose in the body and the external augmentation from insulin sources external to the human body, lack of real time access to computational, communication and command capabilities using a mobile device and the software and databases resident therein, lack of real time access to remote servers and other devices by wired or wireless means to leverage the processing, storage, database and information capabilities resident therein; and other limitations.

The drug delivery including insulin delivery pumps of the prior art are not intelligent and suffer from a number of limitations including inability to wirelessly communicate and relate the drug delivery needs of the body with a number of other factors such as the ingestion of food and physical activity for comprehensive real time control.

Additionally, the non invasive methods of the prior art such as inhalation devices and skin patches are passive methods with no command and control capabilities and of course also lack the communication capabilities with information sources and servers external of the inhalation device, skin patch and other devices thus rendering the delivery of the drug in accurate and independent of valuable collateral information such as the ingestion of food and physical activity. In addition, the prior art does not teach intelligent active skin patch drug delivery systems or intelligent inhalation devices for drug delivery in a controlled and safe manner in conjunction with a host of other relevant information including other health risk factors and gastronomic information.

The prior art additionally does not teach intelligent pain management appliances that can deliver drugs for pain management through catheter means, deliver drugs through skin patch means including delivery through intelligent active skin patches that control drug delivery by stimulating the skin with mechanical, electrical, ultrasound and other means, and do not teach the means for pain management in conjunction with simply providing external stimuli such as electrical pulses/shock and other methods without an associated drug delivery by skin patch or catheter means and further do not teach the means for communication, command and control of intelligent pain management appliances applied at one or more locations of an organ or body locations. The present disclosure teaches the means for pain management by using intelligent pain management appliances that have wired or wireless communication capabilities with a mobile device and one or more servers. The present disclosure also teaches the adaptation of the intelligent skin patches that deliver drugs for different types of pain management applications in a standalone manner or in conjunction with a wearable mobile device including a cellular telephone mobile device.

The present disclosure with specific references to diabetes, blood glucose levels and insulin and the measurement, monitoring and delivery systems thereof is intended to cover a broad range of a number of other health problems and other drugs and is not to be construed as being limited to the specific applications disclosed herein.

SUMMARY OF THE INVENTION

The present application enables mobile devices such as cellular telephones, PDAs, laptop computers and other devices to perform the additional functions of measurement, monitoring and drug delivery for a number of conditions including diabetes. Additionally, a new class of mobile intelligent appliances specifically designed for measurement, monitoring and or drug delivery is disclosed wherein drug delivery, including insulin delivery is by means of a catheter and an external intelligent drug pump appliance; by inhalation of drug/insulin delivery methods and through non invasive methods for diabetes and other applications through intelligent skin patches and intelligent active skin patches. In addition, various methods for pain management in conjunction with different configurations of intelligent appliances and intelligent skin patch systems are disclosed in the present invention.

Ingestion of certain foods, medications and other material such as alcohol, tobacco and non-prescription drugs has a significant bearing on the onset of diabetes in an individual in conjunction with uncontrollable factors such as genetic predisposition. In addition, a significant body of evidence suggests that imbalance of diet, medications, smoking, prescription/non prescription drugs, physical activities, occupational activities, environmental factors, stress and other high risk behavior often have a correlation to the physical and mental health of an individual.

The present invention teaches novel methods and appliances to solve various personal health management problems not addressed in the prior art. Various important objectives of the present invention are enumerated in detail below. Other objectives may become apparent to those knowledgeable in the art and the invention is not to be construed as limited to the specific objectives enumerated herein:

A. Intelligent Personal Health Management Appliances for Blood Glucose Monitoring, Tracking and Real Time Data Analysis:

The incidence of diabetes is significant in adults and juveniles and can be related to the different types of foods ingested and physical activity. There is a real need for controlling the blood sugar level, an indicator of diabetes for maintaining good health. In ability to control the blood sugar levels at times causes diabetic shock, coma or even death. Diabetes is generally exacerbated by excessive body weight. Body weight and blood glucose are controllable by diet. Certain individuals with diabetes are prone to loss of activity in limbs such as toes and consequently certain physical activity that leads to injury is not recommended while safe/controlled physical exercise is advisable. Certain individuals are prone to hypoglycemia and require the quick ingestion of sugar. Therefore, there is a need for an intelligent appliance that is mobile, has significant processing, storage and database, capabilities for measuring, monitoring and controlling blood glucose levels in real time.

1. An objective of the present invention is a wired/wireless blood glucose measurement appliance with the ability for the measurement of blood glucose levels at selected times/time intervals, the tracking of the measured data, the comparison of the measured data with prior history and the correlation of the blood glucose levels with different types of foods ingested and other activities. The blood glucose measurement appliance having the ability for acquiring a sample, for making a measurement, for processing/storing of the software and information in the unit itself, in a server or a combination of the unit and the server. An intelligent blood sugar monitoring appliance that can communicate wirelessly is not available in the prior art.

2. Another objective of the present invention is the capability for configuring a mobile device such a cell phone, a PDA and other mobile devices for the additional functions of a blood glucose measurement, wherein the mobile device acquires a blood sample, analyses the blood for sugar levels and performs said functions in a standalone manner or in conjunction with a local, central and network server. Additionally, the ability to correlate in real time, the measured blood glucose levels with one or more other data such as the medications ingested, food ingested and different types of activities is enabled.

3. A system for blood glucose measurement and tracking in conjunction with a RF ID Tag, including reading information from the RF ID Tag and writing information onto the RF ID Tag in real time or at selected times; further having the capability to use the RF ID Tag and the mobile device individually or together for personal health records and information tracking.

B. Insulin/Drug Delivery System:

4. An objective of the present invention is an intelligent pump for delivery of insulin and other drugs in real time or at selected times including in conjunction with various activities of the individual including food ingestion.

5. An objective of the invention is an intelligent drug delivery pump that operates manually or automatically in conjunction with other intelligent appliances including mobile devices and servers via wired or wireless communication.

6. An objective of the present invention is a specifically designed insulin/drug delivery pump having measurement, monitoring and tracking capabilities.

7. An objective of the present invention is to enable a mobile device such as a cellular telephone, PDA and other mobile devices to perform the additional functions of an intelligent insulin pump; further having the capability for wired or wireless networking with other peripheral devices and servers for information and authentication.

8. An objective of the present invention is to track the blood glucose and other health parameters for infusion of insulin/drug in accordance with the infusion protocols best suited for the individual.

9. An object of the present invention is to correlate the infusion protocols to geographical location for optimal treatment of the personal health of the individual such as in conjunction with a GPS system/server.

10. An object of the present invention is to enable reservoir/cartridge and other mechanisms for infusion of different types of insulin best suited for the condition of the individual including an emergency condition.

Drug Delivery by Inhalation:

11. An object of the present invention is a specially designed intelligent drug/insulin delivery system that is wearable/portable and has wired or wireless networking capabilities.

12. An object, of the present invention is to enable a mobile device such as a cellular telephone, PDA and other devices for performing the additional functions of drug/insulin delivery by inhalation methods.

13. An object of the present invention is a drug/insulin delivery system combining other features such as blood glucose and other parameter analysis and monitoring/tracking.

Drug/Insulin Delivery through Intelligent Skin Patches:

14. An objective of the present invention is a wired or wireless networked intelligent skin patch system for controlled delivery of insulin and other drugs in accordance with drug infusion protocols best suited for the individual in conjunction with other collateral information such as gastronomic information.

15. An object of the present invention is to provide the user the capability to use the skin patch delivery system or the catheter delivery system or both in selected combinations at a selected time based on factors that are specific to the individual.

16. An object of the present invention is an intelligent activated skin patch system that modulates the drug/insulin delivery by one or more skin activation/deactivation methods.

17. An object of the present invention is to enable a skin patch system to operate in a self replenishing mode for continuous use.

18. An object of the present invention is an intelligent skin patch system that maintains a selected concentration level for optimal delivery of the selected drug.

19. An object of the present invention is to enable the delivery of one or more same or different drugs through a skin patch system.

20. An object of the present invention is an intelligent skin patch system configured with a plurality of reservoirs/cartridges for delivery of one or more drugs in a controlled manner.

21. An object of the present invention is an intelligent skin patch system that is controlled for factors such as temperature, humidity and other factors.

22. An object of the present invention is to enable the intelligent skin patch system for disposable or multiple repeated uses in conjunction with disposable or refillable reservoirs/cartridges.

Pain Management Applications:

23. An object of the present invention is to use the intelligent skin patch system or an array of intelligent skin patch systems for pain management at one or more body locations/organs 24. An object of the present invention is to enable the intelligent skin patch system to be activated by one or more methods including electrical, vibration, ultrasound and other methods for providing stimuli to alleviate the pain.

25. An object of the present invention is to enable the delivery of pain killing/pain alleviating medications/drugs through the intelligent skin patch system by one or more methods such as through the skin or by the catheter.

26. An object of the present invention is to enable the user to accurately describe and record various types of pain and the body locations/organs that cause the pain.

27. An object of the present invention is to enable the individual to view a standardized body location/organ and to view the organ from one or more angles and perspectives for accurately pin pointing the pain and further annotating the display with the description of the pain and other information.

28. An object of the present invention is to enable the individual to view a personalized body location/organ and to view the organ from one or more angles and perspectives for accurately pin pointing the pain and further annotating the display with the description of the pain and other information.

29. An object of the present invention is to enable the tracking of pain and relating said pain to one or more factors.

Real Time Measurement, Monitoring, Tracking and Analysis:

30. An object of the present invention is to enable information acquirement by one or more intelligent appliances and enable said information to be archived in one or more data bases locally or across the network for personalized tracking and analysis or for collaborative use with permitted/authorized individuals such as health care providers. The authentication and other functions being performed per user requirements locally on the selected appliance/device or in conjunctions with a server such as a central or escrow server on which said information is securely maintained.

31. An object of the present invention is to enable the user to carry with him/her in wearable or portable format pertinent information for optimal personal health management at any location or at any time including in conjunction with a RF ID Tag, a mobile device, an intelligent personal health management appliance and one or more servers.

Other objects, features and advantages of the present invention will become apparent from the following detailed description when taken in conjunction with the accompanying drawings.

BRIEF DESCRIPTION OF THE EMBODIMENTS OF THE INVENTION

The accompanying drawings, which are incorporated in and form a part of this specification, illustrate embodiments of the invention and, together with the description, serve to explain the principles of the invention:

Figure 4:
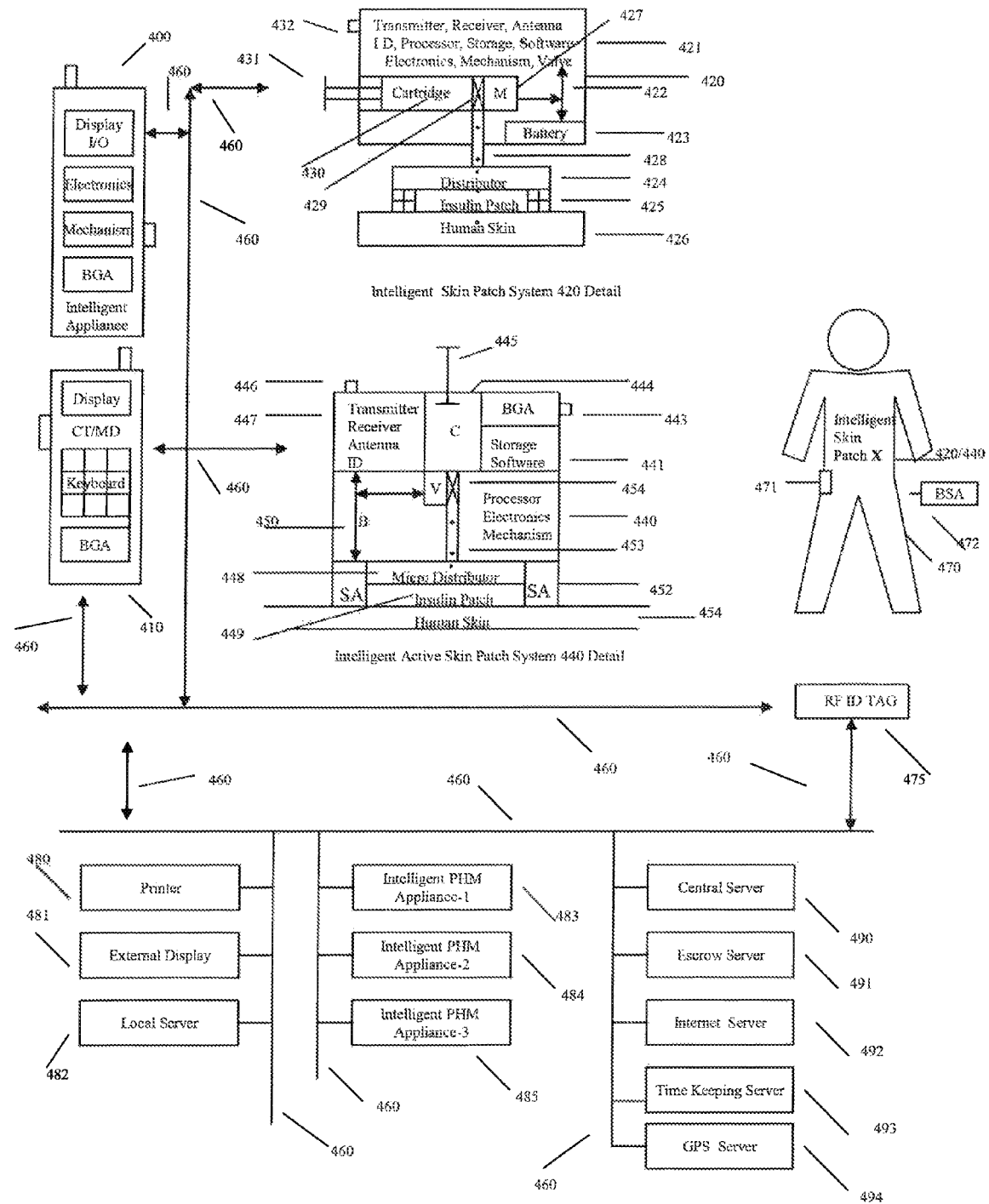

FIG. 4 shows a blood glucose measurement, monitoring and insulin/drug delivery appliance that is automatic or manual wherein the insulin/drug is delivered by two different skin patch means into the individual user, a RF ID Tag identifying the user and a mobile device associated with a user in a wired or wireless networking environment. The illustration shows an intelligent activated skin patch system.

Further, the illustrations in FIG. 4 are also applicable for the management of pain using a catheter for delivering pain medication; and different types of external stimuli such as electrical pulses/shock, ultrasound and other methods used singly or in conjunction with a selected skin patch for delivery of pain medication.

FIG. 5 shows a means for archiving and co-relating various types of information that include various measured values of a health parameter related to the individual and the individuals other activities including gastronomic information.

DETAILED DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the appended claims.

For example, the embodiments that follow relate to a networking architecture, a system and apparatus for enabling personal health management in conjunction with different intelligent appliances that are mobile and or wireless, but are intended to include stationary units as well, such as personal computers (PCs) and stationary intelligent and non intelligent appliances; wherein as an illustration a non intelligent appliance is enabled with an external wireless capability and external networking capability by means of attachments and other methods.

Further, the personal health management inquiry or request can be in any form of intelligence, such as key entries from a keyboard, voice in any language, graphics such as a key click on a graphic page, mouse clicks on a view, or even tactile responses or depressions of a foot pedal. Required translations, such as from one language to another or, from a tactile entry to a voice command, are made automatically.

As another example, personal health management is enabled in conjunction with one or more, types of information including gastronomic information, one or more personal and/or common databases, storage, processors and software resident on one or more devices/servers located within the device itself, a local server, a central server, a network server or located across a network. including the Internet. The architecture system and apparatus may have other applications, for example in a hospital/institutional/professional environment, and the embodiments described herein are for illustrative purposes and are not to be construed as limiting the present invention.

The present invention is a personal health management system comprising of various types of intelligent personal health management appliances that are designed and used for specific personal health management applications. The intelligent personal health management appliances are used in a standalone manner or in conjunction with various gastronomic inquiry and information systems, since the health of an individual generally pivots around the ingestion of food, ingestion of other substances, physical activities and mental activities.

The intelligent personal health management appliance is configured for the real time acquisition of various data related to the individual, storing the acquired data within said appliance and or on a central server, displaying the selected information on said device or another display device, making an information inquiry including health factors and gastronomic factors to an information server having a personal health and gastronomic database. The present invention includes displaying a response to the inquiry related to personal health and gastronomic information from the information server/central server on the selected display device including the intelligent personal health management appliance.

The present invention also includes sending a personal health and or a gastronomic inquiry from the intelligent personal health management appliance/display device to the information server, preparing the selected personal health/gastronomic response to said inquiry on the information server, and receiving the response to the inquiry from the information server with an intelligent personal health management appliance and other devices that include a cellular telephone/a mobile device.

A preferred embodiment includes formatting the personal health/gastronomic-response to the selected inquiry on the display device, and displaying the formatted personal health/gastronomic response to the inquiry on the display device and storing/retrieving said information on one or more databases located on the intelligent appliance itself, on a mobile device such as a cellular telephone, personal digital assistant, lap top computer, other mobile devices, stationary devices and one or more servers such a local server, a central server, a network server and a escrow server.

The escrow server and or other servers securely stores personal health and other information and provides access to the selected information to selected/permitted individuals/entities at the selected times using permission schemes and authentication schemes as defined by the individual. The escrow server further provides that the underlying permission/authentication schemes are not generally made available and are executed by the escrow server without revealing or compromising sensitive personal information.

In the present invention a user selecting an action to be performed by the intelligent personal health management appliance/a mobile device or a stationary device connects to a central server/other, intelligent personal health management appliances of the present invention by wired or wireless means. The central server receives the request for the action, and parses the necessary information to service the information/action request. Reference to the central server is intended to include one or more other servers such a local server, a network server and an escrow server. Any information may be parsed, but will normally include identification (ID) of the user, specific identification information related to the intelligent personal health management appliance, the servers and other devices; information about the selected input/output formats selected, communication protocols selected, language, the basis or type of the action, the number of actions desired, and any parameters that may be pertinent.

The parameters involved may include, for example, inputting a limit on the values for a comparison, such as a limit on a selected health parameter by itself or in relation/conjunction with other parameters including gastronomic parameters. As an example of a parameter, an action related to the intended ingestion of a certain type of food may result in a warning upon comparison with specific health parameter specific to the individual such as the cholesterol level.

Another preferred embodiment of the present invention includes a mobile device such as a cellular telephone, personal digital assistant, lap top computer and other mobile devices for enabling the control of one or more intelligent personal health management appliances and servers, for initiating a selected query/action using the user preferred input/output methods, displaying a response to the inquiry from the information server/other intelligent appliances on the display device/mobile device/intelligent personal health management appliance.

The preferred embodiment includes sending the inquiry from the display device/mobile device to the information server. The preferred embodiment also includes preparing a response to the inquiry on the information server. The mobile device is used for receiving the response to the personal health management inquiry from the information server with the display device/mobile device. The preferred embodiment includes formatting the response to the personal health management inquiry on the display device/mobile device/personal health management appliance, and displaying the formatted response to the personal health management inquiry on the display device/mobile device/intelligent personal health management appliance.

In another preferred embodiment of the present invention a mobile device such as a cellular telephone, PDA or other mobile communication devices are additionally enabled for performing one or more functions of an intelligent personal health management appliance. As an example a cellular telephone is enabled for performing the functions of a blood sugar measurement/monitoring appliance for providing real time control over the insulin level/blood sugar level of an individual, especially in conjunction with the real time ingestion of the various foods ingested by the individual and the physical/mental activities related to the individual.

Figure 1:
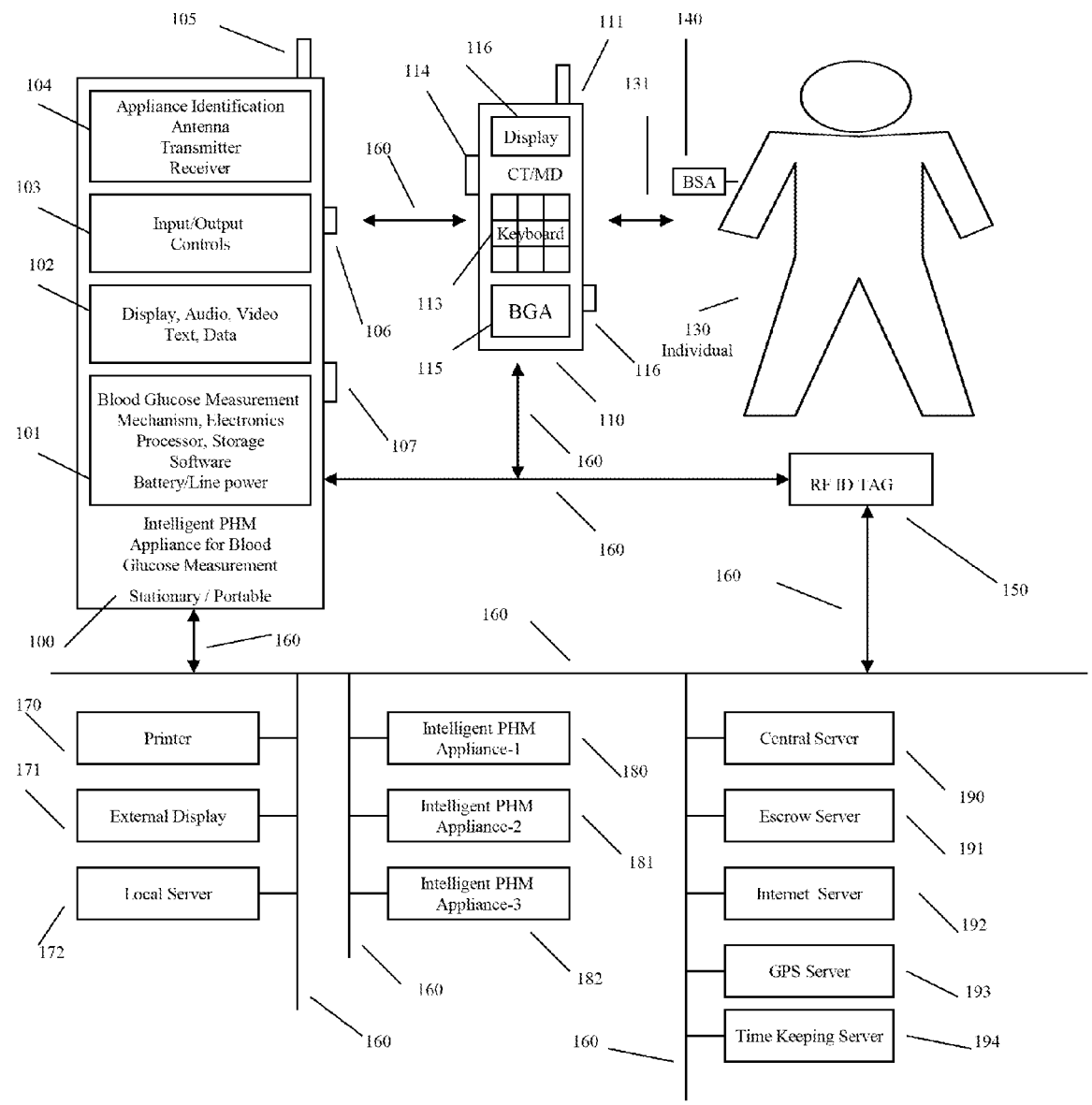
FIG. 1 shows a blood glucose measurement and monitoring appliance, a RF ID Tag identifying the user and a mobile device associated with a user in a wired or wireless networking environment.

The novel embodiments and teachings of the present invention will be made clear in conjunction with the figures and the descriptions:

Referring now to FIG. 1, a blood glucose measurement appliance 100, specially designed for stationary/portable intelligent blood glucose measurement, monitoring and tracking applications is disclosed. The intelligent personal health management glucose measurement and monitoring appliance 100 comprises of the functional block 101 consisting of the measurement mechanism, electronics, processor, storage, software, power supply including line and battery power; a functional block 102 for enabling display, audio, video, text and data; a functional block 103 enabling different types of input/output and controls; and a functional block 104 consisting of appliance identification including static IP, mobile IP, an imbedded or externally attached RF ID and other identification methods, a transmitter/receiver and an internal antenna and or an external antenna 105. The appliance 100 further comprises of a port 106 for external plug ins of attachments/communication leads and a port 107 for inserting a blood sample strip for enabling the analysis of the blood sugar levels of the individual within the appliance 100 in conjunction with the blood chemistry analysis capability of the chemical sample strip 140 on which a blood sample is acquired by pricking the body at a selected location of the individual 130. The appliance 100 is enabled for wired or wireless communication with mobile devices 110 other intelligent personal health management appliances 180, 181 and 182 and a central server 190, an escrow server 191, an Internet server 192, a global positioning GPS server 193 and a time keeping server 194 by means of the communication path 160. In addition the appliance 100 is enabled for communication with other peripheral devices such as a printer 170, an external display 171 and a local server 172. The communication path 160 enables wired or wireless communication between different devices/appliances and servers by one or more communication protocols appropriate for each specific communication. The individual 130 is uniquely identifiable by one or more methods including in conjunction with an external or imbedded RFID Tag 150 and a mobile device 110. The mobile device 110 further comprises of a keyboard 113, a display 116, an antenna 111, an external port 114 and a blood sugar analysis 115 capability by one or more methods including in conjunction with the blood sample strip 140. The mobile device 110 in this illustration is enabled with additional capabilities and functions for executing blood glucose measurement, monitoring and tracking. The mobile device is intended to include a cellular telephone CT, a PDA, a lap top computer and other mobile communication and computation devices. The mobile device has the capability for voice and data communication on one or more channels using one or more inputs/outputs, one or more transmitters/receivers, and one or more processors. The individual user may select a preferred input and output for communication, command and control which includes voice, speech, audio, video, graphics, photos and data and other forms.

ILLUSTRATIVE EXAMPLE 1

Use of the Intelligent Personal Health Management Blood Glucose Measurement Appliance The appliance 100 is designed for wearable and stationary applications by itself. A blood sample is acquired by the individual by pricking the body at a selected location in conjunction with a blood sample acquisition device 140 and a chemical strip which is subsequently inserted into the blood glucose measurement appliance 100 such as through the port 107. The strip/disc is analyzed internally by the blood glucose measurement mechanism 101. The processed data is archived within the appliance 100, itself such as in one or more storage media and related data bases. The individual 130 is enabled to input his/her own identification, ID, password or some other manual means to uniquely identify and relate the data to the specific individual. The individual is further enabled to utilize one or more selected input methods for command and control and also use same or different methods of output including a touch screen or other display. Upon measurement at a selected time and at a selected location, the measured vales are presented on the appliance 100 in a selected manner. Additionally, the measured values and other information resident within the appliance 100 is communicated to one or more other intelligent personal health management appliance for collaborative management of the personal health of the individual; and also communicated to one or more servers for collaborative and comprehensive analysis of one or more factors that potentially have an impact on the individuals health.

ILLUSTRATIVE EXAMPLE 2

Use of the Intelligent Blood Glucose Appliance in Conjunction with a Standard Stationary/Mobile Device Additionally, the individual enabled with a standard stationary/mobile device such as a personal computer, cellular telephone, PDA, lap top computer and other mobile devices is enabled to communicate with the appliance 100 by wired or wireless means for the purpose of command and control; and for the purpose of using the processing power/storage/software and databases resident on the stationary/mobile device/servers in a collaborative manner; and for updating and sharing one or more related and unrelated databases resident therein. A special figure for a standard mobile device is not shown but it is inferred by referring to the specially configure mobile device 110 that is shown in FIG. 1 The individual is identified by automatic recognition of the identity of the mobile device by the appliance 100 for secure communication between the appliance 100 and one or more appliances/servers/devices.

A related factor for treatment and control of diabetes and other devices is the ingestion of various types of food, the quantity of the foods ingested and the frequency at which certain foods are ingested. The measured blood glucose values are therefore enabled for co-relation with a number of other factors. The appliance 100 is intended for stationary, portable and mobile applications with the ability to communicate voice, data and other information on one or more input/output channels of communication using a plurality of communication protocols.

ILLUSTRATIVE EXAMPLE 3

Use of the Intelligent Personal Health Management Blood Glucose Measurement Appliance, in Conjunction with a RF ID Associated with the Individual The RF ID 150 uniquely associated with a specific individual 130, such as by wearable or imbedded means, comprises of the ability to read information from the RF ID or has the added capability for read and write onto the RF ID device. The appliance 100 has the ability to therefore communicate automatically with the RF ID 150 to send an alert, such that a self blood glucose test must be performed. The appliance 100 also is enabled to communicate an alert to the individual 130 by vibration, audible, visible and other signaling means. The RF ID 150 is enabled for communication with other devices such as a mobile communication device including a cellular telephone, PDA, lap top computer, other personal health management devices, peripheral devices and servers for communicating information and or receiving command and control instructions.

ILLUSTRATIVE EXAMPLE 4

Use of a Mobile Device Configured for Performing the Additional Functions of Intelligent Blood Glucose Measurements Mobile device such as a cellular telephone, PDA, lap top computer and other mobile/and even stationary devices such as personal computers are enabled for performing the additional functions of blood glucose measurement and monitoring. Such a specifically configured mobile device 110 has the additional capability for the insertion of a blood sample strip 140, through a port 116 wherein the blood glucose analysis module 115 measures the specific blood glucose levels for archival within the database of the mobile device itself or for communication to one or more other intelligent personal health management appliances 180, 181, 182, servers 190, 191, 192, 193, 194 and 172 and peripheral devices such as external display 171/printers 170 and the RFID Tag 150. In this illustrative embodiment of the present invention one single mobile device performs communication, computation, command, control and measurement/monitoring tasks related to a specific health factor such as diabetes/blood sugar measurement or one or more other personal health factors and their respective measurement/monitoring tasks.

Figure 2:
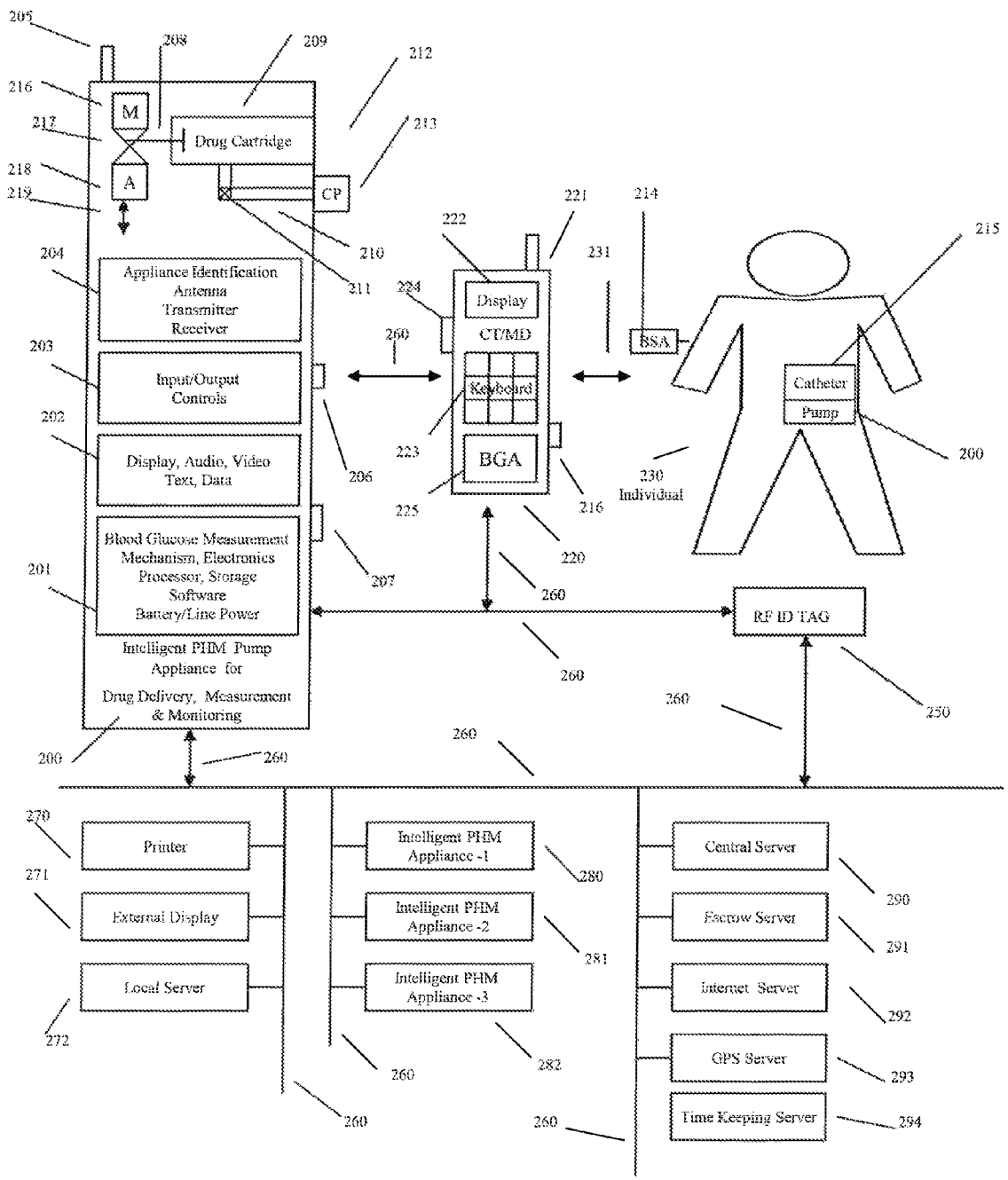
FIG. 2 shows a blood glucose measurement, monitoring and insulin/drug delivery appliance that is automatic or manual wherein the insulin/drug is delivered by catheter means into the individual user, a RF ID Tag identifying the user and a mobile device associated with a user in a wired or wireless networking environment.

Referring now to FIG. 2, the individual 200 is central to the system and represents the person seeking to manage one or more aspects of his/her own personal health including the means for obtaining information, for managing the information and for taking the selected action at the selected time. The individual is enabled for uniquely identifying himself/herself by a plurality of input/output means including voice, speech and text in one or more languages, a unique user ID number, a unique password, biometric methods and other methods. The biometric authentication information related to the individual is maintained by the intelligent appliance 200, by the mobile device 220, the RF ID Tag 250, the central server 290 and the escrow server 291 and other devices/servers to enable a layered secure authentication system wherein one or more specific authentication information is separated from other authentication information to thwart identity theft or unauthorized use.

While FIG. 1 of the present invention teaches a measurement and monitoring system only, however, there is a need for an intelligent drug delivery system/pump for the treatment of diabetes and other health conditions. FIG. 2, addresses this need for controlled and real time drug delivery by teaching in a preferred embodiment of the present invention, an intelligent drug delivery system with specific focus on insulin delivery for the treatment of diabetes. However, the drug delivery systems of the present invention are equally applicable by extension for other types of drug deliveries for various other health conditions.

Referring to FIG. 2 in detail, an appliance 200 for blood glucose measurement, monitoring and insulin delivery comprises of an intelligent appliance for personal health management, drug delivery, monitoring and measurement. The appliance 200 comprises of a functional block 201 performing the functions of a blood glucose measurement mechanism, electronics, processor, storage, software and battery/line power; a functional block 202 consisting of means for display, audio, video, text and data; a functional block for input/output and controls; a functional block 204 for appliance identification, user identification, transmitter/receiver and antenna. The reference to said functional blocks is for illustrative purposes and those knowledgeable in the art may organize the essential functions in one or more ways using one or more functional blocks and electrical, electronics and mechanical components and subsystems. In addition the appliance 200 a drug cartridge or a drug reservoir 209, a tube 210 by which, the drug contained in the reservoir/cartridge flows to the catheter port CP 213 via a control one way check valve 211. The one way control check valve ensures that the drug, which in the case of diabetes treatment is insulin, does not flow in the reverse direction back into the cartridge/reservoir to limit contamination of the contents of the cartridge/reservoir.

The cartridge/reservoir is enabled for manual infusion by selecting the manual M 216 option by the individual 230 for delivery/infusion of the drug/insulin by the movement of a plunger 208 such that the drug is released from the cartridge/reservoir in graduated quantities into the tube 210 and subsequently sent via the valve 211 and the catheter port 213 to the catheter 215 containing an external needle/soft canula, which is not shown in where in said needle/canula is inserted into the fatty tissue of the individual in a selected location of the body such that the drug/insulin passes into the blood stream of the individual 230 in a controlled manner. In a similar manner, the individual 230 may select the automatic option A 218 wherein a micro motor contained within the functional block is actuated by electrical signals, delivered through the communication path 219, for enabling the controlled movement of the plunger 208 for delivery of the drug to the catheter port via the tube 210 and the valve 211. Alternately, the automatic selection enables the controlled opening and closing of the valve 211.

Additionally, the appliance 200 is provided with a port 206 for plugging in peripheral leads/appliance; and a port 207 for the insertion of a blood sample acquisition BSA strip 214. The appliance 200 is enabled for wired or wireless communication with servers 272, 290, 291, 292, 293, and 294; and other intelligent personal health management appliances 280, 281 and 282; and one or more peripheral equipment 270 and 271; and, a mobile device 220 and an RF ID Tag 250 associated with the individual 230 via the communication path 260 using one or more communication protocols, one or more processors, one or more antennas and one or more input and output ports.

The mobile device 220 may be a standard communication and or computation related mobile device or a specifically configured mobile device for performing one or more of the additional functions enumerated for the appliance 200. Thus the appliance 200 is enabled for operation in a standalone manner or in conjunction with a standard mobile device or a mobile device configured for performing the additional functions of measuring, monitoring and drug delivery. The mobile device 220 comprises of communication, computation, command and control capabilities for voice and data information using one or more communication protocols by means of a keyboard and display and related features. Optionally, the mobile device 220 is configured with a blood glucose analysis or other analysis capabilities including drug delivery capabilities.

ILLUSTRATIVE EXAMPLE 5

Use of an Intelligent Insulin Drug Delivery Pump Appliance

Referring once again to FIG. 2, the intelligent appliance 200 performs the measurement, monitoring and insulin pump functions in conjunction with the individual 230 and the individual's requirements. The individual 230 measures his/her blood glucose level by pricking the body, acquiring a blood sample on a blood sample strip and subsequently inserting said sample strip into the port 207 of the appliance 200; wherein the blood glucose level is analyzed automatically and the results compared against a preset value for one or more selected or automatic actions. The measured value/results are also presented/displayed for review by the individual 230 and stored, within the database of the device and/or communicated externally of the appliance 200.

Upon determination by the individual that the measured values of the blood glucose levels warrant the infusion of a selected amount of insulin into the individual 230's body, the individual activates the manual mechanism M 216 and plunger 208 to infuse/inject a controlled amount of insulin into the body. The quantity and time at which the insulin was injected is stored by manual input or automatic input means in a database within the appliance 200 or in other databases external of the appliance 200. The individual 230 is enabled to relate the amount of and the types of foods ingested to the measured blood glucose values to infuse the recommended/selected amount of insulin into the body. Thus the individual is able to regulate in real time the insulin levels within the body for dynamic diabetes management.

Alternately, the measured blood glucose levels are automatically compared within preset values for determining the infusion levels of insulin best suited for the individual and his/her infusion protocol established in conjunction with selected health professionals and historic and contemporaneous information related thereto including gastronomic information, blood pressure, ECG and other information. The selected amount of insulin in accordance with the preset insulin injection protocols or manually selected protocols is automatically injected by mechanism A 218 which receives a signal for graduated movement of the plunger 208 and or the graduated opening of the check valve 211 ensuring that the selected/prescribed qty of insulin is injected at the selected time. The quantity of insulin infused and the time at which it was infused is automatically recorded in one or more databases including within the appliance 200, a mobile device 220, a RF ID Tag 250 and one or more other intelligent personal health management appliances 280, 281 and 282 and servers 272, 290, 291, 292.

The geographical location at which the insulin infusion was effected is accurately determined in conjunction with a global positioning capability/GPS server and the accurate time at which the infusion was effected is also recorded in conjunction with built-in time keeping capabilities of the, appliance 200 or the mobile device 220 or a time keeping server 294. The change in blood glucose levels and its relationship to gastronomic and other information, the amount of infusion of insulin, the frequency of infusion of insulin and other factors are co-relatable in the time domain including geographical position domain and with other personal health risk factors enabling the individual to proactively manage his/her personal health wherever he/she may be and in whatever time zone they may be.

In addition, one or more reservoirs/cartridges of insulin are enabled optionally within the appliance 200, such that the infusion of fast acting, slow acting and other types of specially formulated insulin infusions are enabled for one or more conditions including an emergency condition such as diabetic shock, coma and other life threatening conditions. Further the appliance 200 is enabled to communicate manually or automatically to certain preset alarm levels and hazard levels to activate one or more user selected emergency protocols.

ILLUSTRATIVE EXAMPLE 6

Use of an Intelligent Insulin Drug Delivery Pump Appliance in Conjunction with a Standard or Specially Configured Mobile Device A mobile device such as a cellular telephone, PDA and other mobile devices are enabled to communicate in a proximate communication mode with the wearable intelligent pump appliance 200. The communication, computation, command and control capabilities of the mobile device are leveraged by the intelligent pump appliance 200 to enable enhanced processing, storage, software and database capabilities. Similarly, the capabilities of one or more servers are utilized by the intelligent pump appliance 200. In addition, the RF ID Tag 250 is used to read from and or write to information in real time thus providing real time information via the appliance 200 itself, via the mobile device itself, via the RF ID Tag itself, via one or more remote appliances/servers or a combination thereof.

Figure 3:
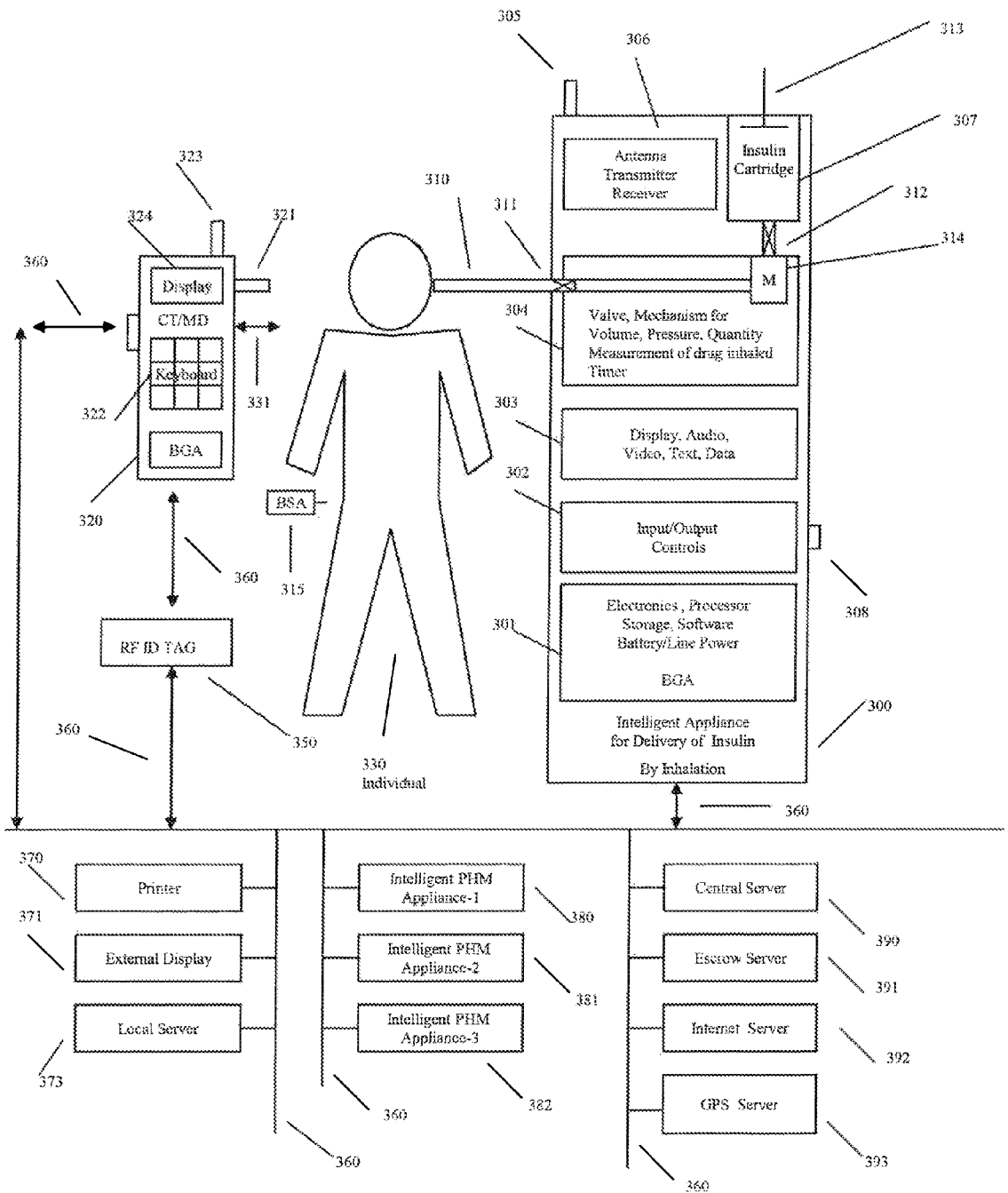
FIG. 3 shows a blood glucose measurement, monitoring and insulin/drug delivery appliance that is automatic or manual wherein the insulin/drug is delivered by inhalation means into the individual user, a RF ID Tag identifying the user and a mobile device associated with a user in a wired or wireless networking environment.

Referring now to FIG. 3 in detail, the ability to deliver drugs through the an inhalation method through nasal passages and the mouth/throat is well known. However, the drug delivery systems consist of spraying a drug substance in an uncontrolled manner through an apparatus that does not provide a means for manually or automatically recording and tracking the amount, frequency and time at which the drug was delivered by these means and further does not enable the drug infusion by inhalation methods to other health factors including gastronomic factors.

A number of preferred embodiments of the present invention overcome the limitations of the prior art inhalation techniques. This is explained in detail by referring to FIG. 3 and the descriptions disclosed herein:

A specifically designed intelligent appliance for delivery of insulin/other drugs 300 comprises of a fimctional block for electronics, processor, storage, software, battery and or line power 301 wherein functional block representation 301 may optionally consist of a blood glucose analysis, BGA capability as indicated in appliance 300, a functional block 302 for enabling different types of inputs/outputs and controls; a functional block 303 comprising of display including touch screen display, audio, video, text and data capabilities; a functional block 304 comprising of a valve mechanism 311 for enabling one way flow of the drug/insulin for inhalation by the individual 330 wherein the drug flow is enabled including means for measuring volume, pressure, quantity, and the duration for which the drug was delivered and the time at which the drug was inhaled by a specific individual 330; a functional block 306 comprising an antenna, a transmitter/receiver, the antenna shown externally as 305; and a functional block 307 consisting of an drug/insulin reservoir or a replaceable/refillable cartridge including a means for manual delivery by injection/depression of a plunger 313 such that the drug/insulin is delivered manually in controlled amounts via the valve 312 or by automatic means by a motorized valve or other means 314. The drug/insulin is inhaled by the individual upon manual or automatic selection by the inhalation tube 310 which is directly inserted into the mouth for delivery to the mucosal walls of the mouth, throat and nose. Alternately the tube 310 with a facial mask, which is not shown enables controlled inhalation via the nose only, via the mouth only or a combination of both. The appliance 300 further comprises of a port 308 for external plug in purposes. The appliance 300 is enabled for wired or wireless communication by the communication path 360 using one or more input/output channels and one or more communication protocols on one or more selected channels.

In an alternate configuration, not shown, the appliance 300 is enabled with a blood glucose or other health parameter definition capability for determining the level of or dosage of the drug to be inhaled.

Once again referring to FIG. 3, the individual 330 is enabled for identification by manual input for authentication and or actuation of the appliance 300. The individual in another embodiment is enabled for authentication and actuation of the appliance 300 by RF ID Tag 350 or mobile device means. The RF ID Tag is readable and or writeable. The RFID Tag contains individual specific information that is preloaded and or periodically updated securely. One or more user selected biometric authentication methods are enabled for operation of the appliances/devices/server and software and database contained therein. The appliance 300, the RF ID Tag 350 and the mobile device 320 are enabled for wired or wireless communication with peripheral devices such as a printer 370, a local server 372, an external display 371; one or more other intelligent personal health management appliances 380, 381 and 382; a central server 390, an escrow server 391 on which secure information may, be maintained, an Internet server 392 and a GPS server 393 and even a time keeping server not shown.

The mobile device 320 may be a standard mobile device not enabled for any health parameter measurement or alternately a specially configured mobile device 320 shown with a blood glucose measurement capability 320 or other health parameter capability. The mobile device 320 is enabled for one or more types of input/output including a keyboard input, a display including a touch screen display. The mobile device 320 may be a cellular telephone CT or a mobile device MD including a lap top computer, a PDA and other communication, computation and control devices. By inference the references to the mobile device or intended to include a stationary device performing one or more similar functions of the mobile device. The blood sample acquisition tool 315 enables a blood sample to be acquired by pricking the selected area of the body of the individual 330 for subsequent insertion and analysis within the appliance 300 or the mobile device 320 for blood sugar determination and the need for insulin inhalation. By inference the BSA 315 function is intended for the acquisition of other types of samples for other types of health analysis and for inhalation of the appropriate drug substance.

ILLUSTRATIVE EXAMPLE 7

Use of a Specifically Designed Intelligent Appliance for Delivery of Drugs/Insulin by Inhalation The individual 330 acquires a sample of blood by pricking his/her body at a selected location wherein optionally the sampling may be automated by enabling the pricking action to be automated, drawing a sample of blood onto a strip, in this present invention, the reference to the strip is intended to include all other forms such as strips, disks, palettes and other methods that enable the sample of blood to be acquired onto a passive or active chemical media which subsequently enables the blood sugar/glucose level to be measured by a blood glucose measuring mechanism by manual and or automatic means. The individual determines his/her blood glucose level in conjunction with the intelligent blood glucose measurement capability built into appliance 300 or an external blood glucose measurement meter such as the mobile device CT/MD 320 which may be enabled with a blood glucose analysis capability. Upon determination manually or automatically in conjunction with the appliance 300 or the CT/MD 320 that the blood glucose level mandates the infusion of insulin of a selected level, the individual 330 inhales the insulin through the tube 310 into the mouth or the nose. The inhalation of the insulin is controlled by the check valve 311 and the amount of insulin released from the reservoir/cartridge 307 is controlled manually by depressing the plunger 313 or a similar mechanism via valve 312 or enabled automatically in conjunction with a motor or other metered release mechanism M 314. The amount, rate, flow, pressure, duration and other insulin inhalation parameters are measured and recorded onto a local storage within the appliance 300 and or communicated externally of the appliance 300 to other intelligent appliances, mobile devices, printers, displays and servers for contemporaneous use or use at a selected time in conjunction with other personal health information including gastronomic information. The input/output may be in any form of intelligence selected by the user. The information and measured blood glucose values and the amount of insulin inhaled and other parameters are archived locally and or externally including in a mobile device that is proximately present with the individual 330.

EXAMPLE 8

Use of a Mobile Device CT/MD that is Configured with a Blood Glucose Analysis Capability and an Insulin Inhalation Capability Alternately, the user 300 is enabled to use the standard CT/MD 320 for enabling pass through communication in conjunction with the appliance 300, for storage/retrieval of data contained within the mobile device and for other health management functions to augment the capabilities of the intelligent insulin inhalation appliance 300. In another preferred embodiment of the present invention, a mobile device such as a cellular telephone, PDA and other devices are configured with the additional capabilities for blood glucose analysis and inhalation capabilities contained therein. The user 330 utilizes the CT/MD 320 in a manner similar to the functioning of the intelligent appliance 300 and is enabled to perform one or more other functions contemporaneously or sequentially on one or more input/output channels using one or more selected communication protocols. The RFID Tag 350 is enabled for use independently or in conjunction with the mobile device 320 and or the intelligent inhalation appliance 300. Other control, storage and authentication tasks may be performed independently by the intelligent appliance 300 or the CT/MD 320 or in conjunction with the processing, storage, software capabilities of one or more other appliances/devices and servers.

The illustration of the insulin inhalation appliance 300 and the CT/MD 320 configured with BGA and insulin inhalation capabilities was with specific reference to the inhalation of insulin but is, intended to be applicable for other drugs/medications and is not to be construed as limiting to the illustrated examples.

Another novel embodiment of the present invention is an intelligent insulin/drug skin patch. It is well known that drugs/medications pass through the skin and the fatty tissue into the blood stream of individuals.

Prior art technology enables a skin patch that has a coating of the intended drug, the application of said skin patch to the skin of the user at a selected location and ultimately the reliance on the assumed rate at which the drug diffuses out of the patch into the skin and then into the blood stream. In the prior art, the number of parameters that relate to this diffusion of the drug out of the skin patch into the blood stream are not controlled in real time and are totally dependent on static models derived from a number of individuals and may have no relevance to the specific individual or his/her personal health factors.

Consequently there is a need for an improved intelligent skin patch for controlled and optimal delivery of drugs through the skin based on dynamic needs and specifically suited for the individual. The present invention embodies and teaches two different intelligent skin patches. Other variations and configurations thereof can be made by those knowledgeable in the art in conjunction with the teachings of the present invention and the invention is not to be construed as being limited to the illustrations presented herein.

1. Intelligent Skin Patch System:

Referring now to FIG. 4 in detail, an intelligent skin patch system 420 is described in detail. The intelligent skin patch is affixed to the skin by adhesives or enabled additionally to be strapped on by belt mechanism for secure and continuous contact of the skin patch with the individual's skin. The intelligent skin patch appliance 420 comprises of an insulin skin patch 425, shown with grid marks for highlighting the drawing, providing contrast for illustrative purposes, which makes contact with the skin 426. The case of the appliance 420 further comprises of transmitter/receiver, antenna 432, appliance ID, processor, storage, software, electronics, mechanism together illustrated as 421; a cartridge/reservoir 430 with a manual plunger 431, a valve 429 through which insulin or other drugs are enabled for delivery via the tube 428 to the distributor 424 which evenly spreads the drug over the entire surface area of the skin patch 425. A battery 423 is shown for internal power supply. It should be understood that the external power supply not shown but is enabled by inference. The communication bus between different components within the intelligent skin patch 420 is shown as 422. This bus may be wired or wireless.

For enabling automatic release of insulin from the reservoir to the skin patch a micro motor M 427 or other automated means is enabled in conjunction with a valve 429 or other controlled metering mechanism. The system 420 is enabled simply as a skin patch with a reservoir and no manual plunger capability or with a manual plunger capability included. The illustration shows a cartridge/reservoir with a plunger but the option without a manual plunger is inferred.

Alternately for manual release of the insulin to the skin patch a plunger that forces insulin out of the cartridge/reservoir 430 is enabled. This novel design and system of the present invention for delivery of insulin and other drugs via the skin patch is unique and is not available in the prior art. This system in the present invention is referred to as intelligent skin patch system since there is no provision in this configuration to stimulate the skin.

EXAMPLE 9

Use of the Intelligent Skin Patch System in Conjunction with a Blood Glucose Testing Appliance/Monitor Referring once again to FIG. 4, the individual 470 determines at a selected time his/her blood glucose level in conjunction with a standard blood glucose measurement/monitor device [not shown] or an intelligent blood glucose appliance 400. The appliance 400 is similar to the intelligent blood glucose measurement/monitoring appliances illustrated in prior figures FIG. 2 and FIG. 3 and for reasons of brevity it need not be described in detail. The appliance 400 is used in conjunction with the acquisition of a blood sample via the BSA 472 or other means.

Upon determination that the measured values of the individual warrant the infusion of insulin from external sources, the individual chooses the skin patch method and applies the intelligent skin patch system 420 that has been described in detail above. The system 420 may be held to the skin with an adhesive, such adhesive being part of the skin patch, or applied separately. This adhesive ensures that the skin patch is held in intimate contact across its entire surface to the skin of the individual 470. Alternately, the system may additionally be strapped to the skin by means of a belt or other mechanism for secure and continuous contact with the skin and continuous infusion of insulin to the blood stream by infusion via the skin/fatty tissue.

The intelligent blood glucose appliance 400 may provide the blood glucose measured values to the individual by visual, voice or other intelligence means for the individual 470 to initiate the application of the system 420 to the skin and activate the system 420; or the system may be strapped on at the outset to the individual at a selected body location and the intelligence is automatically provided from the appliance 400 to the intelligence skin patch system 420 for activation of the system 420 and the initiation of the delivery of insulin through the system 420.

As an example, in the event the measured blood glucose level is higher than a preset value then the appliance 400 transmits a wired or wireless communication signal to the intelligent skin patch system 420 for a controlled release of insulin best suited for the individual and his/her specific protocols or for a standardized release of insulin in conjunction with normalized insulin delivery protocols for an individual of that type of demographics such as age, sex and other factors. The signal sent from the appliance 400 is received by the antenna 432, and the receiver; the transmitting appliance 400 and the system 420 are enabled for recognition by their identification ID to ensure that the correct instructions are being provided to the intended system 420 from the appliance 400. Similarly, a cellular telephone, PDA, lap top computer and other mobile devices represented by 410 are enabled for command and control or alternately for command and control inclusive of blood glucose measurement and monitoring capabilities. The individual's health profile and individual specific information including insulin infusion protocols are enabled within the appliance 400 or the mobile device 410 either of which may be used by the individual 470 in conjunction with the intelligent skin patch system. Additionally, certain selected individual specific health information and insulin infusion protocols are enabled within the skin patch system 420 and enabled for operation with its processor, storage, software and other capabilities. Thus the intelligent skin patch system operates in conjunction with a specifically designed intelligent blood glucose measurement and monitoring appliance 400, a mobile device 410, a RF ID Tag 473 which is enabled for reading information from and or writing information to; one or more servers 490, 491, 492, 493 and 494, and one or more intelligent appliances 483, 484 and 485, a local server 482, external display 481 and a printer 480. The communication between the enumerated servers, devices and intelligent appliances is enabled by one or more wired or wireless communication paths using one or more communication protocols as represented by the communication path 460. The intelligent skin patch system thus is enabled for operation using its own processing, storage, software, data base wired/wireless communication capabilities or in conjunction with the processing, storage, database, software and wired/wireless communication capabilities resident within an intelligent appliance 400, a mobile device 410, one or more servers including time keeping, global positioning and other servers for delivery of insulin to the individual at the selected time and in a selected geographical location in selected dosages that are specific to the individual. Further the intelligent skin patch system 420 is thus able to communicate/interact for various forms of information and intelligence such that the delivery of insulin is coordinated in conjunction with collateral information that includes gastronomic information [gastronomic factors such as the types of foods ingested and the times at which the foods are ingested may have significant impact on the production of insulin by the body and the amount of insulin needed at any given time by the body]. The intelligent skin patch system of the present invention is novel and has significant utility further having real time communication and control capabilities and for synergistically operating with information contained within or external of the system. Prior art systems have no forms of intelligence or any communication, capabilities let alone real time communication capabilities.

The intelligent skin patch system 420 when used in the automatic mode is enabled for controlled delivery of insulin by a micro motor or other delivery mechanism 427 wherein the motor 427 is controlled in conjunction with the processor and electronics contained therein.

EXAMPLE 10

Use of the Intelligent Skin Patch System for the Additional Function of Delivery of Insulin through a Catheter in Conjunction with the Skin Patch or Independent of the Skin Patch The delivery of insulin through the skin is slower compared to the delivery of insulin through direct infusion methods such as through a catheter that is inserted into the fatty tissue/blood stream of the individual. At times diabetics may require a quick infusion of significant and controlled quantity of insulin which is not physically possible through a skin patch whether the skin patch is intelligent or not Therefore, in an alternate embodiment of the present invention; the intelligent skin patch system is enabled for the additional function of direct infusion of drugs/insulin through a catheter port [not shown], wherein the catheter port is part of the system 420 and enables an external catheter 471 to be attached to the catheter port of the system 420. The individual 470 is enabled with a catheter 471 for delivery of insulin by direct infusion method such that the catheter 471 is enabled for attachment to a catheter port of the system 420. The insulin thus is enabled to flow from the system 420 through the catheter 471 into the individual 470. In this configuration, the individual is enabled for operating a plunger 431 to infuse a graduated amount of insulin from the reservoir/cartridge through the catheter into the body. This additional amount of insulin may be in lieu of or in addition to the amount of insulin being released slowly through the skin patch.

The intelligence of when to use the alternate method of catheter infusion may be provided by the intelligent skin patch system which is enabled for using the measured values of the blood glucose in conjunction with a range of health parameters in a standalone manner or in communication with other servers, mobile devices and appliances external of the system 420; or in the case of inability to measure and the perception/judgment by the individual that a controlled and graduated amount of insulin must be quickly infused in critical situations that diabetics often face.

Thus the novel features of the present invention enable the intelligent skin patch system to be used in a plurality of ways that include the skin patch method of drug/insulin delivery and the catheter method of drug/insulin delivery or a controlled combination of both methods. The prior art does not enable such capabilities for controlled and intelligent delivery of drugs/insulin through intelligent skin patches nor does it teach a skin patch system that has the additional dual capability for delivery of drugs/insulin in conjunction with a catheter.

EXAMPLE 10

Use of the Intelligent Skin Patch in a Self Replenishing Mode to Augment the Supply of Drugs/Insulin within the Skin Patch Normally, skin patches are formulated with a certain predetermined amount of drug/insulin contained therein, which at the projected rate of delivery and absorption through the human skin lasts for a defined length of duration. The limitation of this static approach to drug delivery through the skin patches is that the rate at which drugs including insulin are absorbed through the skin is variable and is different for different individuals and their body chemistries and physical factors. The rate of absorption is also dependent on the location of the body at which the skin patch is applied. Environmental factors such as extreme dryness/lack of humidity may also effect the evaporation/loss by other factors and the absorption through the skin since even the physical factors related to the skin are altered by these environmental and body chemistry/physical conditions. Consequently, there is a need for a skin patch that is self replenishing to provide continuous uninterrupted delivery.

In a preferred embodiment of the present invention, the drug/insulin skin patch 425 is enabled for maintaining a selected concentration level of the drug/insulin within the skin patch, including a constant or variable concentration level of the drug/insulin. This novel feature is accomplished in the present invention in conjunction with a reservoir/cartridge of the drug/insulin 430 which through the valve 429 and the delivery tube 428 and the distributor 424 enables a constant amount of micro drops of the drug/insulin to be delivered to the insulin skin patch 425 such that the concentration level of the drug/insulin is constant and or at a selected concentration level. The ability to measure/sense the concentration level of the drug within the skin patch and to provide this information to the processor such that the valve 429/ motor 427 are intelligently controlled and to enable said communication for control purposes is enabled by the communication path 422. Consequently, a selected rate at which the drug/insulin is provided is enabled automatically with a feed back loop of a measured value of the drug/insulin within the patch, a selected control value and the means for automatically metering a selected quantity of the drug/insulin to maintain said selected control value. Of course, the means for delivering the drug/insulin at a controlled metered rate without measuring the concentration value of the drug/insulin within the skin patch is by default enabled.

In addition, the intelligent skin patch system 420 is enabled optionally to measure humidity, temperature including skin temperature and ambient temperature and other environmental and individual related biological factors such that the rate/quantity/time/frequency at which the drug/insulin is delivered is fine tuned to the geographical location and ambient conditions in which the individual is present and specific measured biological parameters that are specific to the individual. In addition, the intelligent skin patch 420 is enabled with internal intelligence and communication capabilities such that the controlled delivery of the drug/insulin through the skin patch and or a catheter method is controlled in conjunction with a number of factors that include gastronomic, personal health, geographical location, internal body parameters and external environmental parameters for comprehensive personal health management of the individual in real time or at selected times; including in conjunction with a mobile device/stationary device.

EXAMPLE 11

Use of the Intelligent Skin Patch System for Refillable Applications or Disposable Applications The intelligent skin patch system 420 may itself be used in many ways.
1. Use the entire intelligent skin patch assembly 420 one time and at the end of its useful life dispose of the entire system including the mechanism, electronics and the skin patch; and the reservoir/cartridge in the case where this option is enabled.
2. Use the entire skin patch assembly 420 multiple times and simply change the skin patch 425 only.
3. Use the cartridge/reservoir 430 only once and dispose of the cartridge/reservoir at selected interval of time or upon sensing the absence or low concentrations of the drug/insulin.
4. Use the cartridge/reservoir multiple times by enabling a safe refill capability for addition/removal of the drug/insulin, including sanitizing the cartridge/reservoir or one or more parts of the assembly 420.
5. Enable the intelligent skin patch system 420 for delivery of one or more different drugs/different concentration of said drugs that include different types of insulin such that the system 420 or parts thereof can be used for multiple uses and the drugs/insulin delivered through the skin and or by means infusion through a catheter.
6. Enable the intelligent skin patch system 420 with multiple skin patches that are constructed and organized such that one or more drugs are sequentially or contemporaneously delivered. An example of a skin patch organization is concentric annular rings of different drug containing patches contained within a single larger skin patch. Other types of skin patch organizations are possible by extension.
7. Enable an intelligent skin patch system 420 with multiple micro cartridges/reservoirs where in a selected cartridge/reservoir contains a selected drug, thus enabling different drugs to be delivered through a common skin patch or different skin patches for the individual to manage multiple personal health factors; including enabling delivery of different drugs from different cartridges/reservoirs by skin patch delivery method and or catheter delivery method.

The above different configurations and uses of the intelligent skin patch system as embodied in the present invention are useful, unique and novel and not taught by the prior art. The figures appended to this specification including FIG. 4 readily enable the teaching of the above outlined uses 1-7 and other uses and separate figures are not deemed necessary to illustrate these different configurations.

Referring once again to FIG. 4, another unique embodiment of the present invention is a novel variation of the intelligent skin patch system 420, specifically illustrated as an intelligent active skin patch system 440. The novel features of the intelligent active skin patch system 440 include significant similarities to that of 420 but additionally include the ability to activate the skin by a plurality of means for increased/controlled absorption of drugs/insulin through the human skin. Of course all references to skin patches are intended in the present invention animals by extension.

As described in extensive detail above with reference to system 420, the human skin is an active entity that modulates its behavior and characteristics based on a number of body/individual dependent and external factors. The pore size of the skin is affected by cold and heat resulting in the pores closing or opening and increased blood flow or decreased blood flow; and also affecting body temperature.

These and other factors either limit or accelerate the absorption of various drugs through the skin. Thus the ability to externally control the behavior/characteristics of the skin provide another added control means for efficient drug delivery through the skin wherein by appropriate stimulation of the skin or lack there of the rate/nature of delivery of a drug through the skin can be accelerated or slowed down. A novel embodiment of the present invention is an intelligent active skin patch system 440 that leverages the additional control capabilities for drug delivery through a skin patch by a skin activation, SA mechanism 452. The SA mechanism 452 activates the skin by one or more selected methods used singly or in combination. The system 440 is configured with selected skin activation methods or a combination of skin activation methods. These skin activation methods include:
1. Varying the temperature of the skin by applying heat or cold. As an example heat may be generated by electrical resistance means in conjunction with the battery power source contained within intelligent skin patch system 440 [battery not shown for keeping the figure less cluttered] and applied to the skin. Cold can be generated by blowing air across the skin or by other methods including cryogenic means. Alternately, the temperature of the cartridge/reservoir may be controlled to enable heating and cooling of the drug itself such that the skin patch and skin temperature is as a result controlled.
2. Providing controlled mechanical agitation or stimulation of the skin by a vibration or other methods wherein the mechanical vibration is enabled by the power source and other mechanisms contained within the assembly 440.
3. Providing controlled sound waves including sound waves at one or more frequencies including ultrasound frequencies using the appropriate sound transducers or other methods within the assembly 440 in conjunction with its electrical, electronic and mechanical, power supply and other capabilities to activate/deactivate the skin in a controlled manner.
4. Providing controlled electrical signals of various frequency, intensity, power, current and voltage such that the skin is activated/deactivated. The internal power supply and electronics of system 440 enable this capability
5. Providing optical/light source[s] of different or varying characteristics and duration such that the skin is activated/deactivated.
6. Providing one or more different methods for activation/deactivation and control of the skin used singly or in selected combinations best suited for the selected drug to be delivered for the selected physical/biological characteristics of the individual and the environment/geographical location that the individual is in.

Referring once again to FIG. 4, particularly intelligent active skin patch system detail 440, the system comprises of one or more functional blocks wherein the functional blocks are for ease of illustration and are not intended to be assumed as rigidly organized as thus, said functional blocks including an antenna 446 shown externally, a functional block 447 including a transmitter, receiver, antenna, system ID; an internal wired or wireless communication path/bus shown as 450; an external wired or wireless communication capability 460; a cartridge/reservoir 444 with an optional plunger 445; a functional block 441 containing software and storage; a functional block 453 consisting of processor, electronics, and mechanism; a valve mechanism 454, a delivery tube 453 or similar means for drug delivery to the skin patch 449 that is internal of the assembly 440; a micro distributor 448 that enables even delivery of the drug across the skin patch 449, the skin shown as 454 and finally the skin activation mechanism SA 452. The skin activation mechanism in conjunction with the internal electronics, processor, mechanisms, storage, software and other capabilities delivers the selected skin activation/deactivation methods to the skin that include mechanical, vibration, sound including ultra sound, electrical impulses and various other forms/methods delivered singly or in selected combinations best suited for the individual.

The system 440 is illustrated with a blood glucose analysis and measurement capability contained therein. However, this BGA 443 capability may be optional and the blood glucose measurement capabilities of an external intelligent appliance such as appliance 400 may be used or the capabilities of a mobile device such as 410 may be used in a configuration of 440 wherein the BGA capability is not present or in addition to it. The intelligent active skin patch system 440 may additionally be used in a manner as illustrated for system 420 with the optional or additional capability for using the catheter method for drug delivery using a catheter port [not shown] contained within the assembly 440 and a catheter 471. Thus the individual 470 is enabled to use the intelligent skin patch system 420 and or the intelligent activated skin patch system 440 in a standalone manner or in conjunction with one or more intelligent appliances 483, 484 and 485; an external display 481, a printer 480, a local server 482, a central server 490, an escrow server, an Internet server 492, a time keeping server 493 and a global positioning system/server 494 using wired or wireless communication for managing diabetes and other personal health ailments in real time using the extensive personal health and other collateral information/capabilities resident within the individual's mobile device 410, the RF ID Tag 475 and other wearable intelligent appliances such as appliance 400.

The present invention has illustrated in detail various appliances/apparatus and systems for real time personal health management with special reference to diabetes. However, the disclosure is valid for a range of other health factors.

EXAMPLE 12

Use of the Intelligent Active Skin Patch System

The operation of the intelligent active skin patch system 440 is similar to that of the intelligent skin patch system 420 except that the skin is activated/deactivated by one or more methods in a controlled manner for optimal drug delivery and absorption. The individual 470 having manually determined that there is a need to activate the skin is enabled to choose one or more methods such as mechanical vibration ultrasound vibration, heat and other methods to enhance the absorption of the drug from the skin patch to the individual. The user is enabled to select the skin activation/deactivation method or alternately the system 440 in a standalone manner or in conjunction with another intelligent appliance/mobile device determines the parameters of the skin activation/deactivation. The activation/deactivation and the intensity, duration and other, parameters of the activation/deactivation are enabled for determination and control in conjunction with a number of parameters related to the individual including gastronomic information. The intelligent skin patch system 420 or 440 are enabled for control by the individual locally using a selected input/output method such as voice, touch, keypad or other methods or controlled in conjunction with an external device such as a mobile device.

Use of Skin Patch Systems and Modified Skin Patch Type Systems for Pain Management:

EXAMPLE 13

Use of the Intelligent Skin Patch System 420 or the Intelligent Active Skin Patch system 440 for Pain Management Certain types of pain are controllable by infusion of selected drugs in .a localized area where the pain is prevalent or by enabling the drug to be absorbed by the blood stream through the skin for general control of the pain. A preferred embodiment of the present invention enables the individual to use one or more same or different types of intelligent skin patches applied at one or more locations of the individual's body for the intelligent real time management of pain wherein the appliance[s] 420/440 operates in a standalone manner or in conjunction with an external device such as mobile device 410 for command and control tasks. There may be a series/plurality of intelligent skin patches used at the same time for the management of the same pain, similar pain or dissimilar pains at one or more locations such that each intelligent skin patch is controlled in conjunction with a mobile device/server or used independently. The information required for the selected, intelligent skin patch system 420/440 to operate in a specific manner best suited for the individual is enabled by the internal software/databases of the appliance 420/440 or the mobile device in conjunction with a central server and other intelligent devices. The information transmitted by the intelligent skin patch 420/440 is enabled for use internally or in conjunction with an external device/server/appliance.

Application of certain selected external stimuli such as electrical pulses/shock, ultrasound, vibration,: and other methods is intended to control and manage the intensity, frequency and the incidence of pain experienced by the individual using the intelligent active skin patch system 440. The ability of the system 440 to deliver the activation/deactivation stimuli to the area of the pain is enabled with an optional design of 440 that does not contain a skin patch or a standard design that contains the skin patch. In addition various features such as a catheter for delivery of the drug are also optionally enabled. The ability to provide, heat, cold, electrical pulses/shock and ultrasound energy to a localized area via a method not containing a skin patch or with a skin patch method enables the individual to control the pain by one or more selected methods. The ultrasound method may treat pain that is internal to the body and not just at skin level. The ultrasound energy may be modulated and adjusted to treat pain at the skin surface or at a selected depth from the skin for treating various types of pains that are deep in the body.

EXAMPLE 14

Visual Mapping of Pain in Conjunction with a Mobile Device and an Information Server In another embodiment of the present invention, the level of pain, the intensity of pain, the duration of pain and the location of pain and other factors in one or more body locations and organs is enabled for being recorded by voice or other methods including by image, graphics and other methods. Health care providers would like to know these details to discern if the pain is life threatening or general in nature. A pain in the heart/chest cavity may be due to gas, heavy lifting or due to a heart attack. Recording in real time or at selected time such valuable information related to pain is of significant value. A preferred embodiment of the present invention is to enable the individual to use a mobile device such as a cellular telephone, PDA, lap top computer or other devices for recording all relevant information related to pain including pain related to a specific organ or different body locations. Said pain related information is enabled for recording in a tabular format, look up tables or in a database format or other formats for further relation to other factors pertaining to the individual such as gastronomic information, exercise and other factors. In another preferred embodiment of the present invention, a two dimensional, three dimensional, cross-sectional and other views of the selected organ are presented to the individual in a display format such as on a touch screen such that the individual can with accuracy pin point the source[s] of pain for informed recording in a database and for real time communication or communication at a selected time with trained health professionals. In another preferred embodiment of the present invention, the individual may select one or more icons to indicate the nature of the pain for ease of description, recording and communication.

Certain pains may radiate out from a center point, certain pains may radiate in from the periphery, certain pains may be pulsating and other pains may have descriptions that are not easily describabable with planar or three dimensional geometric representations such as dull pain, a throbbing pain, a steady pain and other subjective but valuable descriptions. However, the present invention enables the individual to select certain pre defined geometric patterns that describe the specific nature of pain or define customized pain icons that are specific to the individual or use predefined/customized word descriptors.

As a specific example, the individual experiencing pain in the intestinal tract may communicate via the mobile device 410 with an information server that provides a two or three dimensional graphics image of a standard human intestinal tract on the display of the individual's mobile device/stationary device. The individual is enabled to rotate or otherwise manipulate the graphics image of to locate an area that he/she can select by touch sensitive means to exactly pin point the location of the pain and further select one or more other icons that indicate different types of pain patterns. Thus enabling the individual to accurately record various pain symptoms including by voice means and precisely communicate them to a trained health professional.

Pain Management, with Visualization of Body Locations and Organs Exhibiting Pain:

EXAMPLE 15

Pain Management in Conjunction with Visualization of Organs

Another specific example is the visualization of the heart in three dimensions and the ability to rotate/slice and other wise manipulate the image of the heart for recording/annotating the pain felt by the individual at one or more locations in the selected organ or body locations. Similarly other organs may be visualized for determining pain accurately. The nature of the pain, the location of the pain and the relationship of the pain to a time line wherein other related activities such as food ingestion have taken place enables the individual to determine whether the pain warrants emergency response or response at a later time/selected time or is worth ignoring. Pain and its occurrence may have certain patterns which are therefore co-relatable with other factors. For example certain people suffer from migraine headaches but not all their headaches are happenstance, they are in some cases related to the ingestion of foods such as chocolates, coffee and other factors.

Thus the present invention enables the individual to accurately track pain, describe pain, visualize pain in one or more graphical images of specific organs/body locations and relate their pain to a number of factors in real time or over a time period wherein statistically trends may be established.

EXAMPLE 16

Pain Management in Conjunction with Visualization of the Individual's Own Organs In another embodiment of the present invention, the individual is enabled to view his/her own organ[s] rather than a standardized organ of an unknown person or a graphical model of the organ. As an example, the individual who has undergone a thallium contrast magnetic resonance image study of the heart may capture the images of his/her heart in action at a selected time when such a study was undertaken, save said graphics/video images in a secure database such as on a central server, an escrow server or even a mobile device. Upon experiencing heart pains he/she is enabled to select the image from within the mobile device storage/database or down load it from a server, manipulate it, annotate the video/graphics image with notes to indicate pain location and other factors, thus creating a living visual personal health record that is of significant value in personal health management. The selected information is enabled for collaboratively being viewed by the individual and the health professional such that in the event the pain is life threatening, a selected dose of the drug that is pertinent to such treatment is administered by the individual himself or by the health professional in conjunction with a wearable drug delivery system such as the intelligent skin patch system 420 or 440 ensuring that the drug is delivered for certain selected conditions through the skin and for other selected conditions through the catheter. By extension, other types of intelligent measurement, monitoring and drug delivery systems may be used for treatment of the medical condition independently or in conjunction with standardized or personal visual images of the relevant organ. The present invention takes away the exclusivity of personal health records such as X ray, MRI images for health care professional's use only and makes them readily available by wired or wireless communication means to the individual for active personal health management including using said images, graphics, data, video and other information for pain management and other personal health care applications via a mobile device such as a cellular telephone, PDA, lap top computer, a stationary device, an intelligent appliances and servers.

Referring now to FIG. 5, a personal health management record for an individual is shown containing information related to the date and time at which various measurements, monitoring and other activities take place or are intended to take place. As one example the health management record may be organized in one or more formats whereas a tabular format is shown for illustrative purposes. Such a table may contain the measured values of the blood glucose BG level of an individual at one or more points in time including a control value or a normal value. The table may also shown the food ingestion activity such as the type, quantity, location and other information related to the food ingested by the individual including alcohol, tobacco and other substances. The location may be at home or at a restaurant including a fast food restaurant. In addition, the table may contain information related to the types of medications, the dosage/quantity and the times at which said medications are ingested. Further, the table may additionally contain physical/mental activity information such as the type, duration and other information such the calories expended. The information such as the personal health symptoms, duration and type may be included in the table. The times and dosages of the insulin infused by various methods is also recorded. The general and specific actions taken by the individual acting by him/her self or in conjunction with an intelligent appliance, a mobile device, a stationary device, a server and a health professional may also be recorded. The information also may contain individual identification, health care provider information, insurance information, RF ID information, mobile device information, emergency contact information and all other information that is relevant and useful. The tabular format is for illustrative purposes but the intention is that the information may be recorded in one or more databases organized in one or more formats including look up tables for easy reference. The information is intended to be maintained locally within the local processor/storage and or within another intelligent appliance, mobile device, stationary device and one or more servers for use singly or in combination by wired or wireless communication.

The foregoing descriptions of specific embodiments of the present invention have been presented for purposes of illustration and description. They are not intended to be exhaustive or to limit the invention to the precise forms disclosed, and it should be understood that many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A method comprising:
receiving a specimen from a body of a user via a port of a device;
analyzing the specimen and generating processed information via a processor wherein the analyzing includes correlating parameters of the specimen with one or more of biological parameters and health information of the body;
automatically determining a location of the device and outputting information of the location;
making an information inquiry to an information server via the processor, the information server having the health information of the body which includes gastronomic information which is displayed to the user via the device;
idenfifying the user via biometric authentication information related to the user which is maintained at least by each of the device, a central server, and an escrow server such that specified authentication information of the user is separated from other authentication information of the user such that authentication of the user is layered to provide a secure authentication system; and
controlling a delivery system of the device via the processor to administer at least one composition for use in treating the body, wherein the composition is administered under control of the processed information.

2. The method of claim 1, wherein the administering includes one or more of automatically administering and administering under manual control of the user.

3. The method of claim 1, wherein the processed information includes a plurality of dosages corresponding to the parameters of the specimen, wherein the composition is administered under at least one of the plurality of dosages.

4. The method of claim 1, comprising generating control signals one or more of automatically and in response to an input from the user, Wherein the control signals are configured to control one or more of devices coupled to the body, devices implanted in the body, devices coupled to the processor and the administering.

5. The method of claim 4, wherein the processed information includes information of the at least one composition, wherein the information of the at least one composition includes one or more of composition identification information, an amount released, and a time of release.

6. The method of claim 4, comprising a reservoir coupled to the processor, wherein the reservoir is configured to contain at least one composition for use in treating the body.

7. The method of claim 1, wherein the composition is administered as one or more of a liquid, an atomized liquid, and a vapor.

8. The method of claim 1, wherein receiving the specimen includes one or more of receiving a substrate that includes the specimen and automatically taking the specimen from the body.

9. The method of claim 1, wherein the specimen comprises a substrate that includes a blood sample, wherein the processed information includes one or more of an insulin level and a glucose level of the blood sample.

10. The method of claim 1, comprising one or more of transmitting and receiving one or more of the processed information, the biological parameters, and the health information.

11. The method of claim 1, wherein the analyzing includes distributed analyzing among the device or at least one remote device.

12. The method of claim 1, comprising displaying one or more of a raw version and a processed version of one or more of the biological parameters, the processed information, and the health information.

13. The method of claim 1, comprising receiving biometric identification information of the user, the biometric identification information including one or more of voice signals, photographic data, handwriting data, finger print data, and retinal data.

14. The method of claim 1, comprising conmmnicating with a plurality of health management devices, wherein the biological parameters acquired by the health management devices are received by the device.

15. The method of claim 14, comprising controlling the health management devices.

16. The method of claim 1, comprising receiving control data from a remote device, wherein the control data controls one or more of the analyzing and the administering.

17. The method of claim 1, comprising receiving identification information of the user from a remote device.

18. The method of claim 17, comprising one or more of receiving from and transmitting to the identification device one or more of the health information and the biological parameters.

19. The method of claim 1, comprising authenticating one or more of the device and the user.

20. The method of claim 1, comprising communicating alert information in response to the processed information, wherein the alert information includes one or more of a message, a visual alert, an audible alert, and a vibratory alert communicated to the user, wherein the alert information includes one or more of voice data, text, graphics data, multimedia information, and an electronic signal transmitted to a remote device located one or more of on the body, in a home, in an office, and at a medical treatment facility.

21. The method of claim 1, wherein the biological parameters include one or more of current and historical biological information of the user comprising one or more of weight, height, age, body mass index, medical analyses results, body fluid analyses, blood analyses results, electrical activity of the body, heart activity, heart rate, and blood pressure.

22. The method of claim 1, wherein the health information includes one or more of current and historical health information of the user, wherein the health information includes one or more of dietary data, types of food consumed, amounts of food consumed, medications consumed, times of food consumption, physical activity, exercise regimen, work schedule, activity schedule, and sleep schedule.

23. The method of claim 1, wherein the analysis includes correlating one or more of parameters of the specimen, the health information, and the biological parameters with categorical data of the user, wherein the categorical data includes one or more of data of an age category of the user, data of a body type of the user, and parametric data of the user.

24. The method of claim 1, comprising outputting one or more of results of the analysis, the biological parameters, and the health information, wherein results of the analysis comprise suggestions regarding one or more of dietary data, types of food to be consumed, amounts of food to be consumed, medications to be consumed, times food is to be consumed, physical activity, exercise regimen, activity schedule, sleep schedule, and changes to the health information to improve health of the user.

25. The method of claim 1, comprising converting one or more of data of the specimen, the biological parameters, and the health information from a first form to a second form.

26. The method of claim 1, comprising correlating one or more of the biological parameters, the health information, the processed information, and the administering of the at least one composition to the body with the information of the location to one or more of adjust administration of the composition to the body and recommend actions for controlling health of the body, wherein the recommended actions include one or more of actions of food ingestion, medication ingestion, and physical activity.

27. The method of claim 1, wherein the processed information includes one or more administration parameters of the administered composition, the administration parameters including composition, quantity, volume, pressure, rate, flow, temperature, and duration of administration.

28. A non-transitory computer readable medium including executable instructions which when executed in a processing system provide drug delivery by:
   receiving a specimen form a body of a user via a port of a device;
   analyzing the specimen and generating processed information, wherein the analyzing includes correlating parameters of the specimen with one or more of the biological parameters and health information of the body
   automatically determining a location of the device and outputting information of the location;
   making an information inquiry to an information server via the processor, the information server having the health information of the body which includes gastronomic information which is displayed to the user via the device;
   identifying the user via biometric authentication information related to the user which is maintained at least by each of the device, a central server, and an escrow server such that specified authentication information of the user is separated from other authentication information of the user such that authentication of the user is layered to provide a secure authentication system; and
   controlling a delivery system of the device to administer at least one composition for use in treating the body, wherein the composition is administered under control of the processed information.

29. The method of claim 1, wherein the device is a mobile device.

30. The method of claim 29, wherein the mobile device is a cellular telephone.

* * * * *